(12) United States Patent
Peskin

(10) Patent No.: US 8,728,546 B1
(45) Date of Patent: May 20, 2014

(54) MEDICAMENT FOR TREATMENT OF CANCER, CARDIOVASCULAR DISEASES AND INFLAMMATION

(71) Applicant: Brian Peskin, Houston, TX (US)

(72) Inventor: Brian Peskin, Houston, TX (US)

(73) Assignee: Swing Aerobics Licensing, Inc., Houston, TX (US)

( * ) Notice: Subject to any disclaimer, the term of this patent is extended or adjusted under 35 U.S.C. 154(b) by 27 days.

(21) Appl. No.: 13/836,179

(22) Filed: Mar. 15, 2013

(51) Int. Cl.
A61K 36/00 (2006.01)

(52) U.S. Cl.
USPC .......................... 424/725; 424/758; 424/768

(58) Field of Classification Search
None
See application file for complete search history.

(56) References Cited

U.S. PATENT DOCUMENTS

| | | | |
|---|---|---|---|
| 5,120,760 | A | 6/1992 | Horrobin |
| 5,223,285 | A | 6/1993 | DeMichele et al. |
| 5,246,726 | A | 9/1993 | Horrobin et al. |
| 5,318,991 | A | 6/1994 | Horrobin et al. |
| 5,374,657 | A | 12/1994 | Kyle |
| 5,411,988 | A | 5/1995 | Bockow et al. |
| 5,466,841 | A | 11/1995 | Horrobin et al. |
| 5,516,801 | A | 5/1996 | Horrobin et al. |
| 5,518,753 | A | 5/1996 | Bracco et al. |
| 5,550,156 | A | 8/1996 | Kyle |
| 5,562,913 | A | 10/1996 | Horrobin |
| 5,583,159 | A | 12/1996 | Horrobin et al. |
| 5,618,558 | A | 4/1997 | Horrobin et al. |
| 5,663,202 | A | 9/1997 | Horrobin et al. |
| 5,709,855 | A | 1/1998 | Bockow |
| 5,888,541 | A | 3/1999 | Horrobin et al. |
| 6,407,075 | B1 | 6/2002 | Scott et al. |
| 6,667,064 | B2 | 12/2003 | Surette |
| 7,001,610 | B2 | 2/2006 | Stewart |
| 7,045,143 | B1 | 5/2006 | Sawatzki et al. |
| 7,390,507 | B2 | 6/2008 | Ruwart |
| 7,638,142 | B2 | 12/2009 | Krawitz |
| 8,053,471 | B2 | 11/2011 | Stahl et al. |
| 8,062,688 | B2 | 11/2011 | Greither |
| 8,211,947 | B2 | 7/2012 | Selman-Housein Sosa |
| 2003/0000391 | A1 | 1/2003 | Highman et al. |

FOREIGN PATENT DOCUMENTS

| | | | |
|---|---|---|---|
| CN | 1270160 | A | 10/2000 |
| CN | 1292411 | A | 4/2001 |
| CN | 1312071 | A | 9/2001 |
| GB | 2 341 317 | A | 3/2000 |
| HU | 9600336 | A2 | 12/1997 |

OTHER PUBLICATIONS

Oleic Acid, available at http://en.wikipedia.org/wiki/Oleic_acid, as retrieved Feb. 3, 2014.*

Berti et al., Echium: A Source of Stearidonic Acid Adapted to the Norther Great Plains in the US, Issues in New Crops and New Uses, 2007, pp. 120-125.

Echium Oil—Refined, 2007, Bioriginal Food & Science, Corp., 2 pages.

Guo et al., "Studies of the Properties and Use of the Seed Oil of *Melia azedarach* L.," Natural Product Research and Development, Biological Resources Institute, Mar. 1995, vol. 7, No. 1., pp. 82-87.

Huang et al., "Preparation of *Camelina sativa* seed oil by cold-pressing and its refining technology," Oil Crops Research Institute, Zhongguo Youzhi, 2006, vol. 31, No. 1, pp. 17-20.

Huang et al., "Study of *Camelina sativa* Seed Oil Preparation by Cold-Pressing and *Camelina sativa* Seed Oil Refining Technique," China Oils and Fats, 2006, vol. 31, pp. 17-20.

Laidlaw et al., "Effects of supplementation with fish oil-derived n-3 fatty acids and γ-linolenic acid on circulating plasma lipids and fatty acid profiles in women," Am J Clin Nutr, 2003, vol. 77, pp. 37-42.

Office Action, dated Dec. 14, 2011, U.S. Appl. No. 12/818,723, 49 pages.

Office Action, dated Apr. 17, 2012, U.S. Appl. No. 12/818,723, 90 pages.

Whelan J., "Dietary Stearidonic Acid is a Long Chain (n-3) Polyunsaturated Fatty Acid with Potential Health Benefits," J Nutrition, Critical Review, 2008, pp. 5-10.

Label of 'Super Omega 6&3 Oils', World Health Mall, Inc., Alpine California, printed Oct. 2013.

Label of 'Jenn RD Supps #EFAS Dietary Supplement', distributed by: Jenny Westerkamp, RD, printed Oct. 2013.

Label of ChouskyCentre, Scientifically-Advanced Nutritional Supplements, Plant-Based Parent Plus GLA Ultimate EFAs, Dietary Supplement, manufactured by ChouskyCentre, printed Oct. 2013.

Label of Power EFAs, Scientifically-Advanced Nutritional Supplements, Dietary Supplement, manufactured for John Bros International, Inc., printed Oct. 2013.

Label of 'parent essential oils—pathway to health, Ultimate EFA's, Dietary Supplement', manufactured by BioAge Ltd, printed Oct. 2013.

Label of 'Cellular Oxygen4Cells.com, Oxygen, Scientifically-Advanced Nutritional Supplements, Parent Essential Oils, Dietary Supplement', manufactured by NRG, Inc., printed Oct. 2013.

'Resellers who requested artwork or Private Labels', printed Oct. 2013.

Label of 'AB Advanced Bionutritionals, Advanced EFA Formula, Essential fatty acids from parent oils, Dietary Supplement', distributed by Advanced Bionutritionals, printed Oct. 2013.

Label of 'Parent Essential Fatty Acids, 4pets2, Canine EFAS—chewable capsules, Plant-Based Parents Plus GLA, Dietary Supplement', distributed by TREN LLC, printed Oct. 2013.

(Continued)

*Primary Examiner* — David J Blanchard
*Assistant Examiner* — Daniel F Coughlin
(74) *Attorney, Agent, or Firm* — Foley & Lardner LLP; Richard Peet; Benjamin A. Berkowitz

(57) ABSTRACT

The invention provides a medicament for the treatment of cancer, cardiovascular diseases and/or inflammation. The medicament may be administered orally, parenterally or topically.

16 Claims, 1 Drawing Sheet

(56) References Cited

OTHER PUBLICATIONS

Label of 'Parent Essential Fatty Acids, 4pets2, Kitty Doggy EFAS—Liquid, Plant-Based Parents Plus GLA, Dietary Supplement', distributed by TREN LLC, printed Oct. 2013.
Label of 'Yes™, Scientifically-Advanced Nutritional Supplements, Ultimate EFAs, Plant-Based Parents Plus GLA, Dietary Supplement', distributed by TREN LLC, printed Oct. 2013.
Label of Cardio Crusader—For the Young at Heart, Scientifically-Advanced Nutritional Supplements, "Parent" Essential Oils, Dietary Supplement, manufactured for Cardio Crusaders, printed Oct. 2013.
Label Cardio Crusader—For the Young at Heart, 45-day supply, Scientifically-Advanced Nutritional Supplements, "Parent" Essential Oils, Dietary Supplement, manufactured for Cardio Crusaders, printed Oct. 2013.
Label of 'Yes™, Dietary Supplement', manufactured by Your Essential Supplements, Inc., printed Oct. 2013.
Label of Energy: Scientifically-Advanced Nutritional Supplements, Ultimate EFAs, Dietary Supplement, 120 capsules, manufactured for Successboeken.nl, printed Oct. 2013.
Label of Energy: Scientifically-Advanced Nutritional Supplements, Ultimate EFAs, Dietary Supplement, 236 ml, manufactured for Successboeken.nl, printed Oct. 2013.
Label of PEFA, Parent Essential Fatty Acid, nutritional supplement, Made in the U.S.A, printed Oct. 2013.
Label of 'PEO, Parent Essential Oils, nutritional supplement, 756 mg', manufactured by Your Essential Supplements, Inc., printed Oct. 2013.
Label of 'PEO, Parent Essential Oils, nutritional supplement, 725 mg', made in the U.S.A., printed Oct. 2013.
Label of 'Healthy for Life, Natural Omega 3 6 9, Dietary supplement, 725 mg, 120 capsules', manufactured for Healthy for Life, printed from http:///www.healthyforlifeuse.com/media/images/products/omega-label.jpg printed Oct. 2013.
Label of 'Healthy for Life, Natural Omega 3 6 9, Dietary supplement, 8 fluid ozs. (236 ml)', manufactured for Healthy for Life, printed from http:///www.healthyforlifeuse.com/media/images/products/omega-liquid-label.jpg printed Oct. 2013.
Label of "Supplemental Facts from 'Yes™ Ultimate EFS', 1450 mg", retrieved from http://www.yes-suppplements.com/media/catalog/product/cahce/1/image/9df78eab3352d0 printed Oct. 2013.
Label of "Supplemental Facts from 'Yes™ Ultimate EFS', 2.46 mL", retrieved from http://www.yes-suppplements.com/media/catalog/product/cache/1/image/9df78eab3352d0 printed Oct. 2013.
Label of "Supplemental Facts from 'Yes™ Herbal Supplement', 18 mg", retrieved from http://www.yes-suppplements.com/media/catalog/product/cache/1/image/9df78eab3352d0 printed Oct. 2013.
Label of "Supplemental Facts from 'Yes™ Herbal Supplement', 500 mg", retrieved from http://www.yes-suppplements.com/media/catalog/product/cache/1/image/9df78eab3352d0 printed Oct. 2013.
Label of "Supplemental Facts from 'Yes™ Herbal Supplement'", retrieved from http://www.yes-suppplements.com/media/catalog/product/cache/1/image/9df78eab3352d0 pritned Oct. 2013.
Label of "Supplemental Facts from 'Yes™ Whey Supplement'", retrieved from http://www.yes-suppplements.com/media/catalog/product/cache/1/image/9df78eab3352d0 printed Oct. 2013.
Label of "Supplemental Facts from 'Yes™ Herbal Supplement'", retrieved from http://www.yes-suppplements.com/media/catalog/products/cache/1/image/9df78eab3352d0 printed Oct. 2013.

\* cited by examiner

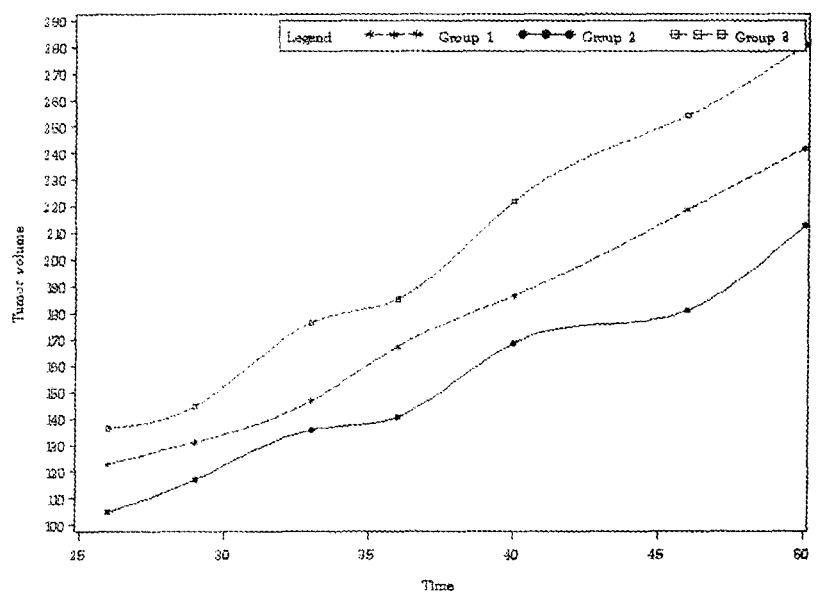

MEDICAMENT FOR TREATMENT OF CANCER, CARDIOVASCULAR DISEASES AND INFLAMMATION

FIELD OF THE INVENTION

The invention relates generally to a medicament and its use for the treatment and prevention of cancer, cardiovascular diseases and inflammation.

BACKGROUND OF THE INVENTION

Although proper dietary and lifestyle habits, routine screening and prophylactic vaccines help reducing the risk for certain cancers, more than 1,000,000 people are diagnosed with cancer every year. The etiology of cancer is multi-factorial, as cancer results from the interaction of genetic, environmental, medical and lifestyle factors. While prostate cancer is the most frequently diagnosed type of cancer, breast cancer and lung cancer are also common, followed by colorectal cancer and renal cancers. Knowledge of cancer genetics helps identifying individuals that are at risk, and developing a treatment tailored to the molecular fingerprint of the disease. Nevertheless, invasive cancer treatment, including surgery, radiotherapy and chemotherapy, is not always successful and is often accompanied by side effects, such as nausea, vomiting, suppression of the immunological system, weakness, suppression of white cells and platelets, hair loss and damage to the cardiovascular system, the kidney and the nervous system.

Cardiovascular diseases, and coronary heart disease in particular, are the leading cause of death in the United States. Dysfunctional conditions of the heart, arteries, and veins, as well as tobacco use, physical inactivity and an unhealthy diet are the major causes leading to the disease. High cholesterol levels, with consequent excess buildup of fat or plaque deposits, may cause narrowing of the arteries and veins that supply blood to the heart and lead to ischemic heart disease and high blood pressure (hypertension). Often, there are no symptoms of underlying cardiovascular diseases and a heart attack or stroke may be the first warning and although early medical detection and treatment is available, the treatment is not always effective. Angiograms, bypass surgery and angioplasty are invasive and traumatic procedures associated with high cost and often requiring additional therapy and/or intervention.

Inflammation, which can be acute or chronic, is part of a complex biological response of vascular tissues to harmful stimuli, such as pathogens, damaged cells, or irritants. The process of acute inflammation is initiated by the activation of resident macrophages, dendritic cells, histiocytes, Kupffer cells and mastocytes, which release inflammatory mediators once their pattern recognition receptors (PRRs) recognize pathogen-associated molecular patterns (PAMPs). Vasodilation and the resulting increased blood flow causes local redness (rubor) and heat (calor), and the increased permeability of the blood vessels results in leakage of plasma proteins and fluid into the tissue (edema), which manifests itself as swelling. Some released mediators increase sensitivity to pain (hyperalgesia, dolor) and alter the blood vessels to permit the migration of leukocytes, mainly neutrophils, into the tissue. Inflammation may also lead to loss of function. Prolonged inflammation, known as chronic inflammation, leads to a progressive shift in the type of cells present at the site of inflammation and is characterized by simultaneous destruction and healing of the tissue from the inflammatory process. Current therapies for inflammation and pain are often palliative, with limited effectiveness and side effects. In addition, diagnosis of chronic inflammatory diseases is often made rather late after there is irreversible organ damage and they often require invasive procedures.

Accordingly, there is an urgent need in the art for alternative, non-invasive therapies, that make use of natural compositions that effectively modulate immune response and effectively prevent and treat cancer, cardiovascular diseases and inflammation. The present invention satisfies this need.

SUMMARY OF THE INVENTION

It is therefore an object of the invention to provide solutions to the aforementioned deficiencies in the art.

It is an object of the present invention to provide a therapeutic composition for the prevention and treatment of cancer, cardiovascular diseases and inflammation.

It is a further object of the invention to provide methods for treating or preventing cancer, cardiovascular diseases and/or inflammation in a subject in need thereof.

Thus, in one embodiment, the invention provides a medicament comprising a composition comprising a blend of oils comprising linoleic acid (LA) and α-linolenic acid (ALA) in a LA/ALA ratio that is greater than 1:1 and less than 5:1. In one aspect of the invention, the oils in the composition comprise between about 15% and about 85% of gamma linolenic acid (GLA)-containing oils. In a preferred aspect of the invention, the composition comprises less than 0.5% arachidonic acid.

In one embodiment, the oils in the composition further comprise an eicosapentaenoic acid (EPA) and/or docosahexaenoic acid (DHA)-containing oil. Preferably, the combined amount of EPA and DHA in the composition is less than the amount of GLA. Even more preferably, the ratio between GLA and the combined amount of EPA and/or DHA is from 1:1 to 5:1. In a preferred aspect of the invention, the combined amount of EPA and DHA in the composition is less than the amount of GLA. Preferably, the amount of EPA and/or DHA in the composition is from about 1.0 mg to about 15.0 mg. Even more preferably, the ratio between EPA and DHA in the composition is from about 1:1 to about 3:1.

In a preferred embodiment, the composition comprises from 0.1% to 25% GLA. In a preferred aspect of the invention, the EPA and/or DHA containing oil is wild salmon or another marine oil selected from the group consisting of fish, krill, squid, mussel, herring and algae.

In yet another embodiment, the oils in the composition are selected from the group consisting of: chia, kukui, echium, flax, pumpkin, soybean, walnut, wheat germ, safflower, sunflower, grape seed, borage, black current, corn, sesame, rice bran, cottonseed, peanut, almond, olive, avocado, coconut, palm kernel, beech, brazil, pecan, pistachio, hickory, filbert, macadamia, cashew, perilla and neem.

In a preferred aspect of the invention, the LA-containing, ALA-containing and GLA-containing oils are chemically unprocessed. In an additional preferred aspect of the invention, the plants or seeds from which the LA-containing, ALA-containing and GLA-containing oils are extracted are not treated with pesticides or additives.

In one embodiment, the composition comprises no more than 70% of a non-essential medium and long-chain fatty acid. Non-essential medium and long-chain fatty acid include, but are not limited to, caprylic acid, capric acid, hendecanoic acid, lauric acid, tetradecanoic acid, myristic acid, myristoleic acid, pentadecanoic acid, pentadecenoic acid, palmitic acid, palmitoleic acid, hexadecanoic acid, hexadecadienoic acid, margaric acid, heptadecenoic acid, stearic acid, oleic acid and vaccenic acid.

Preferably, the LA/ALA ratio in the composition is within a range from 2:1 to 4:1.

In one embodiment, the composition comprises between about 15% and about 85% of evening primrose oil, borage oil, black current oil or another GLA-containing oil and between about 0.1% and about 25% of gamma-linolenic acid (GLA). Preferably, at least 20% of the composition comprises linoleic acid (LA) and α-linolenic acid (ALA) in a LA/ALA ratio that is greater than 1:1 and less than 5:1. In another preferred embodiment, the amount of the DHA and/or EPA in the composition is not greater than 20%.

In a preferred embodiment, the DHA and the EPA are in natural triglyceride form. In one embodiment, at least 50% of the composition by weight comprises linoleic acid (LA) and α-linolenic acid (ALA) in a LA/ALA ratio that is greater than 1:1 and less than 5:1.

In one embodiment, the medicament of the invention comprises about 16.5% evening primrose oil; about 34.5% flax oil; about 16.5% pumpkin oil; about 5.5% coconut oil; about 13.5% sunflower oil; and about 13.5% safflower oil. Preferably the oils in the medicament are chemically unprocessed.

In another embodiment, the medicament comprises about 16.5% evening primrose oil; about 33.0% flax oil; about 22.5% pumpkin oil; about 5.5% coconut oil; and about 22.5% sunflower oil. Preferably the oils in the medicament are chemically unprocessed.

In one aspect of the invention, the composition is in form of a tablet, dragee, gel, powder, soft capsule, hard gelatin capsule, two-piece hard gelatin capsule, particle, pill, granule, baked good, solution, suspension or dispersion for oral or parenteral administration.

In yet another embodiment, the invention provides a method of treating a disease selected from the group consisting of breast cancer, cardiovascular disease and inflammation in a subject in need thereof comprising administering to the subject any of the medicaments of the invention described above. The medicament may be administered orally, enterally, parenterally, intravenously or topically.

The foregoing general description and the detailed description are exemplary and explanatory and are intended to provide further explanation of the invention as claimed. For detailed understanding of the invention, reference is made to the following detailed description of the preferred embodiments, taken in conjunction with the accompanying drawing. Other objects, advantages and novel features will be readily apparent to those skilled in the art from the following detailed description of the invention.

BRIEF DESCRIPTION OF THE DRAWINGS

FIG. 1 is a graph illustrating measured differences in tumor volumes between groups of mice from 26 to 50 days after tumor implantation.

DETAILED DESCRIPTION OF THE INVENTION

Linoleic acid (LA) and alpha-linolenic acid (ALA) are two essential fatty acids that the human body cannot synthesize and must be obtained from food. Once absorbed by the body, linoleic acid and alpha-linolenic acid are then metabolized into eicosapentaenoic acid (EPA), docosahexaenoic acid (DHA) and gamma-linolenic acid (GLA). Routine food processing highly adulterates these essential oils which become harmful when ingested. Furthermore, food and nutraceutical and pharmaceutical composition containing high amounts of marine oils, which are enriched in EPA and DHA, may elicite an inflammatory response.

The invention is based on the unexpected discovery by the inventor that proper administration of a combination of essential fatty acids from essential fatty acid-containing oils in ratios that are based on actual body tissue metabolism, physiology and hormonal balance increases cellular oxygenation, which is prevented in most individuals by the ingestion of processed food containing transfats and/or commercially hydrogenated oils. The inventor has also unexpectedly discovered that minimal amounts of DHA and/or EPA, when combined with GLA, enhance the effectiveness of GLA. Accordingly, the invention provides natural oil compositions that comprise a combination of omega-6 and omega-3 fatty acids, GLA and optionally omega-3 metabolite fatty acids in low dose, to obtain a synergistic effect on cell oxygenation and metabolism, for the treatment of breast cancer, cardiovascular diseases and/or inflammation in a subject in need thereof. The natural oil compositions of the invention comprise no more than trace amounts of arachidonic acid, as it is well known in the art that increased arachidonic acid consumption exacerbates inflammation in individuals with a history of inflammatory diseases or who are in compromised health. By "trace amounts" it is intended that the medicament comprises less than 0.5% arachidonic acid, preferably less than 0.2% arachidonic acid and even more preferably less that 0.1% arachidonic acid by weight of the total composition.

Thus, in one aspect of the invention, DHA and/or EPA are added to the compositions, such that the amount of GLA by weight in the composition is greater than the combined amount of DHA and EPA by weight. The ratio of GLA to EPA/DHA in the composition is 1:1 or greater, preferably 3:1 or greater, and is preferably 5:1. The total amount of EPA and/or DHA in the composition is between 1 and 15 mg, and the composition comprises no more than 20% of DHA or combined DHA and EPA by weight. Salmon oil or wild salmon oil is a preferred source of EPA/DHA. Additional sources of EPA and/or DHA include, but are not limited to, marine oil, such as fish oil, krill oil, squid oil, mussel oil, herring oil and algae-based oil.

The compositions of the invention are devised to meet the fatty acid requirements of the human body. Although extremely fit individuals have a lesser requirement for omega-6 fatty acids because of the cell high efficiency in oxygen transport, most individuals require higher amounts of omega-6 fatty acids and lower amounts of omega-3 fatty acids. Thus, the ratio of omega-6 to omega-3 fatty acids in muscles is from 5.5 to 7.5:1, depending on the level of athletic training. These relationships are shown in the table below.

| | Ratio of Tissue Composition | |
|---|---|---|
| Tissue | Omega-6 (LA) | Omega-3 (ALA) |
| Brain/nervous system | 100 | 1 |
| Organs and other tissues | 4 | 1 |
| Muscles | 6.5 | 1 |

An additional factor that plays a role is the percentage of total body weight of each organ. The brain and nervous system make up about 3% of body weight; the heart, liver, skin and pancreas make up approximately 9% of body weight; and the muscles make up 50% of body weight, as shown in the table below.

| Tissue | Ratio of Tissue Composition | | Percentage of Total Body Weight |
| --- | --- | --- | --- |
| | Omega-3 (ALA) | Omega-6 (LA) | |
| Brain/nervous system | 1 | 100 | 3% |
| Organs and other tissues | 4 | 1 | 9% |
| Muscles | 6.5 | 1 | 50% |

The table below shows the content of omega-6 fatty acids and omega-3 fatty acids composition in seeds.

| OMEGA-6 AND OMEGA-3 COMPOSITIONS OF SEEDS | | | | | | | |
| --- | --- | --- | --- | --- | --- | --- | --- |
| Seeds | Fatty acid percentage in oil | | | | | | |
| | Fat | Polyunsaturated | | | Monounsaturated | Saturated | |
| | Content in | LNA | LA | LNA + LA | | | |
| Name | Seed (%) | 18:3w3 (%) | 18:2w6 (%) | W3 + w6 (%) | 18:1w9 (%) | 18:0 (%) | 16:0 (%) | Total (%) |
| hemp | 35 | 20 | 60* | 80 | 12 | 2 | 6 | 8 |
| chia | 30 | 30 | 40 | 70 | — | — | — | — |
| kukui | 30 | 29 | 40 | 69 | — | — | — | — |
| flax | 35 | 58 | 14 | 72 | 19 | 4 | 5 | 9 |
| pumpkin | 46.7 | 0-15 | 42-57 | 57 | 34 | 0 | 9 | 9 |
| soybean | 17.7 | 7 | 50 | 57 | 26 | 6 | 9 | 15 |
| walnut | 60 | 5 | 51 | 56 | 28 | 5 | 11 | 16 |
| Wheat germ | 10.9 | 5 | 50 | 55 | 25 | 18 | 0 | 18 |
| evening primrose | 17 | — | 81** | 81 | 11 | 2 | 6 | 8 |
| safflower | 59.5 | — | 75 | 75 | 13 | 12 | — | 12 |
| sunflower | 47.3 | — | 65 | 65 | 23 | 12 | — | 12 |
| grape | 20 | — | 71 | 71 | 17 | 12 | — | 12 |
| corn | 4 | — | 59 | 59 | 24 | 17 | — | 17 |
| sesame | 49.1 | — | 45 | 45 | 42 | 13 | — | 13 |
| rice bran | 10 | 1 | 35 | 36 | 48 | 17 | — | 17 |
| cottonseed | 40 | — | 50 | 50 | 21 | 25 | — | 25 |
| rape(canola) | 30 | 7 | 30 | 37 | 54*** | 7 | — | 7 |
| peanut | 47.5 | — | 29 | 29 | 47 | 18 | — | 18 |
| almond | 54.2 | — | 17 | 17 | 78 | 5 | — | 5 |
| olive | 20 | — | 8 | 8 | 75 | 16 | — | 16 |
| avocado | 12 | — | 10 | 10 | 70 | 20 | — | 20 |
| coconut | 35.3 | — | 3 | 3 | 6 | 0 | 91 | 91 |
| Palm kernel | 35.3 | — | 2 | 2 | 13 | 0 | 85 | 85 |
| beech | 50 | — | 32 | 32 | 54 | 8 | — | 8 |
| brazil | 66.9 | — | 24 | 24 | 48 | 24 | — | 24 |
| pecan | 71.2 | — | 20 | 20 | 63 | 7 | — | 7 |
| pistachio | 53.7 | — | 19 | 19 | 65 | 9 | — | 9 |
| hickory | 68.7 | — | 17 | 17 | 68 | 9 | — | 9 |
| filbert | 62.4 | — | 16 | 16 | 54 | 5 | — | 5 |
| macadamia | 71.6 | — | 10 | 10 | 71 | 12 | — | 12 |
| cashew | 41.7 | — | 6 | 6 | 70 | 18 | — | 18 |
| neem | 40 | 1 | 20 | 21 | 41 | 20 | — | 20 |
| Borage | 60 | — | 38 | 38 | 16 | 4 | 10 | 14 |
| black current | 30 | 13 | 47 | 60 | 11 | 2 | 7 | 9 |

*Includes up to 2% GLA—Gamma Linolenic Acid (GLA)

**Includes 9% GLA, borage contains approx. 24% GLA, black current contains approx. 17% GLA.

***Includes up to 5% erucic acid

The medicaments of the invention are made by combining chemically unprocessed and unrefined seed oils from the seeds listed in the above table and optionally a marine oil in the appropriate ratio to meet the body omega-6 and omega-3 fatty acid requirements.

Suitable oils for the medicament of the invention include, but not limited to, chia, kukui, wheat germ, rice bran, cottonseed, olive, avocado, coconut, palm kernel, beech, brazil, pecan, pistachio, hickory, filbert, macadamia, cashew, neem, hemp, chic nut, flax, pumpkin seed, soybean, walnut, evening primrose, borage, black current, safflower, sunflower, grape seed, sesame, rape (canola), peanut, almond, and corn. The oils are preferably chemically unprocessed and the plants or seeds from which the oils are extracted are preferably not treated with pesticides or additives. Examples of oils enriched in linoleic acid include hemp, chic, evening primrose, safflower, sunflower, soybean, walnut, wheat germ, borage, black current, grape seed, kukui, pumpkin, cottonseed, corn and sesame. Examples of oils enriched in α-linolenic acid may include strains of evening primrose oil, borage oil, black current oil, flax oil, hemp oil, chia oil and kukui oil. An anti-oxidant, such as coconut or palm oil, may be added to the medicament in an amount of approximately 5% of the total mixture, by weight. The plant-based oils in the medicament of the invention, have no detectable amounts of arachidonic acids (C20:4), as shown in the tables below.

| | | Sunflower Oil linoleic (approx. 65%) | | | | | |
|---|---|---|---|---|---|---|---|
| Nutrient | Unit | Value per 100.0 g | # of Data Points | Std. Error | tbsp 13.6 g | cup 218 g | tsp 4.5 g |
| Proximates | | | | | | | |
| Water | g | 0.00 | — | — | 0.00 | 0.00 | 0.00 |
| Energy | kcal | 884 | — | — | 120 | 1927 | 40 |
| Energy | kJ | 3699 | — | — | 503 | 8064 | 166 |
| Protein | g | 0.00 | — | — | 0.00 | 0.00 | 0.00 |
| Total lipid (fat) | g | 100.00 | — | — | 13.60 | 218.00 | 4.50 |
| Ash | g | 0.00 | — | — | 0.00 | 0.00 | 0.00 |
| Carbohydrate, by difference | g | 0.00 | — | — | 0.00 | 0.00 | 0.00 |
| Fiber, total dietary | g | 0.0 | — | — | 0.0 | 0.0 | 0.0 |
| Sugars, total | g | 0.00 | — | — | 0.00 | 0.00 | 0.00 |
| Minerals | | | | | | | |
| Calcium, Ca | mg | 0 | — | — | 0 | 0 | 0 |
| Iron, Fe | mg | 0.00 | — | — | 0.00 | 0.00 | 0.00 |
| Magnesium, Mg | mg | 0 | — | — | 0 | 0 | 0 |
| Phosphorus, P | mg | 0 | — | — | 0 | 0 | 0 |
| Potassium, K | mg | 0 | — | — | 0 | 0 | 0 |
| Sodium, Na | mg | 0 | — | — | 0 | 0 | 0 |
| Zinc, Zn | mg | 0.00 | — | — | 0.00 | 0.00 | 0.00 |
| Copper, Cu | mg | 0.000 | — | — | 0.000 | 0.000 | 0.000 |
| Selenium, Se | µg | 0.0 | — | — | 0.0 | 0.0 | 0.0 |
| Vitamins | | | | | | | |
| Vitamin C, total ascorbic acid | mg | 0.0 | — | — | 0.0 | 0.0 | 0.0 |
| Thiamin | mg | 0.000 | — | — | 0.000 | 0.000 | 0.000 |
| Riboflavin | mg | 0.000 | — | — | 0.000 | 0.000 | 0.000 |
| Niacin | mg | 0.000 | — | — | 0.000 | 0.000 | 0.000 |
| Pantothenic acid | mg | 0.000 | — | — | 0.000 | 0.000 | 0.000 |
| Vitamin B-6 | mg | 0.000 | — | — | 0.000 | 0.000 | 0.000 |
| Folate, total | µg | 0 | — | — | 0 | 0 | 0 |
| Folic acid | µg | 0 | — | — | 0 | 0 | 0 |
| Folate, food | µg | 0 | — | — | 0 | 0 | 0 |
| Folate, DFE | mcg, DFE | 0 | — | — | 0 | 0 | 0 |
| Choline, total | mg | 0.2 | — | — | 0.0 | 0.4 | 0.0 |
| Vitamin B-12 | µg | 0.00 | — | — | 0.00 | 0.00 | 0.00 |
| Vitamin B-12, added | µg | 0.00 | — | — | 0.00 | 0.00 | 0.00 |
| Vitamin A, RAE | mcg, RAE | 0 | — | — | 0 | 0 | 0 |
| Retinol | µg | 0 | — | — | 0 | 0 | 0 |
| Carotene, beta | µg | 0 | — | — | 0 | 0 | 0 |
| Carotene, alpha | µg | 0 | — | — | 0 | 0 | 0 |
| Cryptoxanthin, beta | µg | 0 | — | — | 0 | 0 | 0 |
| Vitamin A, IU | IU | 0 | — | — | 0 | 0 | 0 |
| Lycopene | µg | 0 | — | — | 0 | 0 | 0 |
| Lutein + zeaxanthin | µg | 0 | — | — | 0 | 0 | 0 |
| Vitamin E (alpha-tocopherol)[4] | mg | 41.08 | 8 | — | 5.59 | 89.55 | 1.85 |
| Vitamin E, added | mg | 0.00 | — | — | 0.00 | 0.00 | 0.00 |
| Vitamin D (D2 +D3) | µg | 0.0 | — | — | 0.0 | 0.0 | 0.0 |
| Vitamin D | IU | 0 | — | — | 0 | 0 | 0 |
| Vitamin K (phylloquinone)[1] 2358 | µg | 5.4 | 18 | 1.938 | 0.7 | 11.8 | 0.2 |
| Lipids | | | | | | | |
| Fatty acids, total saturated | g | 10.300 | — | — | 1.401 | 22.454 | 0.464 |
| 4:0 | g | 0.000 | — | — | 0.000 | 0.000 | 0.000 |
| 6:0 | g | 0.000 | — | — | 0.000 | 0.000 | 0.000 |
| 8:0 | g | 0.000 | — | — | 0.000 | 0.000 | 0.000 |
| 10:0 | g | 0.000 | — | — | 0.000 | 0.000 | 0.000 |
| 12:0 | g | 0.000 | — | — | 0.000 | 0.000 | 0.000 |
| 14:0 | g | 0.000 | — | — | 0.000 | 0.000 | 0.000 |
| 16:0 | g | 5.900 | 177 | 0.049 | 0.802 | 12.862 | 0.266 |
| 18:0 | g | 4.500 | 177 | 0.102 | 0.612 | 9.810 | 0.202 |
| Fatty acids, total monounsaturated | g | 19.500 | — | — | 2.652 | 42.510 | 0.878 |
| 16:1 undifferentiated | g | 0.000 | — | — | 0.000 | 0.000 | 0.000 |
| 18:1 undifferentiated | g | 19.500 | 177 | 0.425 | 2.652 | 42.510 | 0.878 |
| 20:1 | g | 0.000 | — | — | 0.000 | 0.000 | 0.000 |
| 22:1 undifferentiated | g | 0.000 | — | — | 0.000 | 0.000 | 0.000 |
| Fatty acids, total polyunsaturated | g | 65.700 | — | — | 8.935 | 143.226 | 2.956 |
| 18:2 undifferentiated | g | 65.700 | 177 | 0.456 | 8.935 | 143.226 | 2.956 |
| 18:3 undifferentiated | g | 0.000 | — | — | 0.000 | 0.000 | 0.000 |
| 18:4 | g | 0.000 | — | — | 0.000 | 0.000 | 0.000 |
| 20:4 undifferentiated | g | 0.000 | — | — | 0.000 | 0.000 | 0.000 |
| 20:5n-3 (EPA) | g | 0.000 | — | — | 0.000 | 0.000 | 0.000 |
| 22:5 n-3 (DPA) | g | 0.000 | — | — | 0.000 | 0.000 | 0.000 |

-continued

Sunflower Oil linoleic (approx. 65%)

| Nutrient | Unit | Value per 100.0 g | # of Data Points | Std. Error | tbsp 13.6 g | cup 218 g | tsp 4.5 g |
|---|---|---|---|---|---|---|---|
| 22:6 n-3 (DHA) | g | 0.000 | — | — | 0.000 | 0.000 | 0.000 |
| Cholesterol | mg | 0 | — | — | 0 | 0 | 0 |
| Phytosterols | mg | 100 | — | — | 14 | 218 | 4 |
| Amino Acids | | | | | | | |
| Tryptophan | g | 0.000 | — | — | 0.000 | 0.000 | 0.000 |
| Threonine | g | 0.000 | — | — | 0.000 | 0.000 | 0.000 |
| Isoleucine | g | 0.000 | — | — | 0.000 | 0.000 | 0.000 |
| Leucine | g | 0.000 | — | — | 0.000 | 0.000 | 0.000 |
| Lysine | g | 0.000 | — | — | 0.000 | 0.000 | 0.000 |
| Methionine | g | 0.000 | — | — | 0.000 | 0.000 | 0.000 |
| Cystine | g | 0.000 | — | — | 0.000 | 0.000 | 0.000 |
| Phenylalanine | g | 0.000 | — | — | 0.000 | 0.000 | 0.000 |
| Tyrosine | g | 0.000 | — | — | 0.000 | 0.000 | 0.000 |
| Valine | g | 0.000 | — | — | 0.000 | 0.000 | 0.000 |
| Arginine | g | 0.000 | — | — | 0.000 | 0.000 | 0.000 |
| Histidine | g | 0.000 | — | — | 0.000 | 0.000 | 0.000 |
| Alanine | g | 0.000 | — | — | 0.000 | 0.000 | 0.000 |
| Aspartic acid | g | 0.000 | — | — | 0.000 | 0.000 | 0.000 |
| Glutamic acid | g | 0.000 | — | — | 0.000 | 0.000 | 0.000 |
| Glycine | g | 0.000 | — | — | 0.000 | 0.000 | 0.000 |
| Proline | g | 0.000 | — | — | 0.000 | 0.000 | 0.000 |
| Serine | g | 0.000 | — | — | 0.000 | 0.000 | 0.000 |
| Other | | | | | | | |
| Alcohol, ethyl | g | 0.0 | — | — | 0.0 | 0.0 | 0.0 |
| Caffeine | mg | 0 | — | — | 0 | 0 | 0 |
| Theobromine | mg | 0 | — | — | 0 | 0 | 0 |

Poppyseed Oil

| Nutrient | Unit | Value per 100.0 g | # of Data Points | Std. Error | tbsp 13.6 g | cup 218 g | tsp 4.5 g |
|---|---|---|---|---|---|---|---|
| Proximates | | | | | | | |
| Water | g | 0.00 | — | — | 0.00 | 0.00 | 0.00 |
| Energy | kcal | 884 | — | — | 120 | 1927 | 40 |
| Energy | kJ | 3699 | — | — | 503 | 8064 | 166 |
| Protein | g | 0.00 | — | — | 0.00 | 0.00 | 0.00 |
| Total lipid (fat) | g | 100.00 | — | — | 13.60 | 218.00 | 4.50 |
| Ash | g | 0.00 | — | — | 0.00 | 0.00 | 0.00 |
| Carbohydrate, by difference | g | 0.00 | — | — | 0.00 | 0.00 | 0.00 |
| Fiber, total dietary | g | 0.0 | — | — | 0.0 | 0.0 | 0.0 |
| Sugars, total | g | 0.00 | — | — | 0.00 | 0.00 | 0.00 |
| Minerals | | | | | | | |
| Calcuim, Ca | mg | 0 | — | — | 0 | 0 | 0 |
| Iron, Fe | mg | 0.00 | — | — | 0.00 | 0.00 | 0.00 |
| Magnesium, Mg | mg | 0 | — | — | 0 | 0 | 0 |
| Phosphorus, P | mg | 0 | — | — | 0 | 0 | 0 |
| Potassium, K | mg | 0 | — | — | 0 | 0 | 0 |
| Sodium, Na | mg | 0 | — | — | 0 | 0 | 0 |
| Zinc, Zn | mg | 0.00 | — | — | 0.00 | 0.00 | 0.00 |
| Selenium, Se | µg | 0.0 | — | — | 0.0 | 0.0 | 0.0 |
| Vitamins | | | | | | | |
| Vitamin C, total ascorbic acid | mg | 0.0 | — | — | 0.0 | 0.0 | 0.0 |
| Thiamin | mg | 0.000 | — | — | 0.000 | 0.000 | 0.000 |
| Riboflavin | mg | 0.000 | — | — | 0.000 | 0.000 | 0.000 |
| Niacin | mg | 0.000 | — | — | 0.000 | 0.000 | 0.000 |
| Pantothenic acid | mg | 0.000 | — | — | 0.000 | 0.000 | 0.000 |
| Vitamin B-6 | mg | 0.000 | — | — | 0.000 | 0.000 | 0.000 |
| Folate, total | µg | 0 | — | — | 0 | 0 | 0 |
| Folic acid | g | 0 | — | — | 0 | 0 | 0 |
| Folate, food | g | 0 | — | — | 0 | 0 | 0 |
| Folate, DFE | mcg_DFE | 0 | — | — | 0 | 0 | 0 |
| Vitamin B-12 | µg | 0.00 | — | — | 0.00 | 00.0 | 00.0 |

-continued

Poppyseed Oil

| Nutrient | Unit | Value per 100.0 g | # of Data Points | Std. Error | tbsp 13.6 g | cup 218 g | tsp 4.5 g |
|---|---|---|---|---|---|---|---|
| Vitamin A, RAE | mcg_RAE | 0 | — | — | 0 | 0 | 0 |
| Retinol | g | 0 | — | — | 0 | 0 | 0 |
| Carotene, beta | μg | 0 | — | — | 0 | 0 | 0 |
| Carotene, alpha | μg | 0 | — | — | 0 | 0 | 0 |
| Cryptoxanthin, beta | μg | 0 | — | — | 0 | 0 | 0 |
| Vitamin A, IU | IU | 0 | — | — | 0 | 0 | 0 |
| Lycopene | μg | 0 | — | — | 0 | 0 | 0 |
| Lutein + zeaxanthin | μg | 0– | — | — | 0 | 0 | 0 |
| Vitamin E (alpha-tocopherol) | mg | 11.40 | — | — | 1.55 | 24.85 | 0.51 |
| Lipids | | | | | | | |
| Fatty acids, total saturated | g | 13.500 | — | — | 1.836 | 29.430 | 0.608 |
| 4:0 | g | 0.000 | — | — | 0.000 | 0.000 | 0.000 |
| 6:0 | g | 0.000 | — | — | 0.000 | 0.000 | 0.000 |
| 8:0 | g | 0.000 | — | — | 0.000 | 0.000 | 0.000 |
| 10:0 | g | 0.000 | — | — | 0.000 | 0.000 | 0.000 |
| 12:0 | g | 0.000 | — | — | 0.000 | 0.000 | 0.000 |
| 14:0 | g | 0.000 | — | — | 0.000 | 0.000 | 0.000 |
| 16:0 | g | 10.600 | 1 | — | 1.442 | 23.108 | 0.477 |
| 18:0 | g | 2.900 | 1 | — | 0.394 | 6.322 | 01.30 |
| Fatty acids, total monounsaturated | g | 19.700 | — | — | 2.679 | 42.946 | 0.886 |
| 16:1 undifferentiated | g | 0.000 | — | — | 0.000 | 0.000 | 0.000 |
| 18:1 undifferentiated | g | 19.700 | 1 | 0 | 2.679 | 42.946 | 0.886 |
| 20:1 | g | 0.000 | — | — | 0.000 | 0.000 | 0.000 |
| 22:1 undifferentiated | g | 0.000 | — | — | 0.000 | 0.000 | 0.000 |
| Fatty acids, total polyunsaturated | g | 62.400 | — | — | 8.486 | 136.032 | 2.808 |
| 18:2 undifferentiated | g | 62.400 | 1 | — | — | 136.032 | 2.808 |
| 18:3 undifferentiated | g | 0.000 | — | — | 0.000 | 0.000 | 0000 |
| 18:4 | g | 0.000 | — | — | 0.000 | 0.000 | 0.000 |
| 20:4 undifferentiated | g | 0.000 | — | — | 0.000 | 0.000 | 0.000 |
| 20:5 n-3 (EPA) | g | 0.000 | — | — | 0.000 | 0.000 | 0.000 |
| 22:5 n-3 (DPA) | g | 0.000 | — | — | 0.000 | 0.000 | 0.000 |
| 22:6 n-3 (DHA) | g | 0.000 | — | — | 0.000 | 0.000 | 0000 |
| Cholesterol | mg | 0 | — | — | 0 | 0 | 0 |
| Phytosterols | mg | 276 | — | — | 38 | 602 | 12 |
| Amino Acids | | | | | | | |

Almond Oil

| Nutrient | Unit | Value per 100.0 g | # of Data Points | Std. Error | tbsp 13.6 g | cup 218 g | tsp 4.5 g |
|---|---|---|---|---|---|---|---|
| Proximates | | | | | | | |
| Water | g | 0.00 | — | — | 0.00 | 0.00 | 0.00 |
| Energy | kcal | 884 | — | — | 120 | 1927 | 40 |
| Energy | kJ | 3699 | — | — | 503 | 8064 | t66 |
| Protein | g | 0.00 | — | — | 0.00 | 0.00 | 0.00 |
| Total lipid (fat) | g | 100.00 | — | — | 13.60 | 218.00 | 4.50 |
| Ash | g | 0.00 | — | — | 0.00 | 0.00 | 0.00 |
| Carbohydrate, by difference | g | 0.00 | — | — | 0.00 | 0.00 | 0.00 |
| Fiber, total dietary | g | 0.0 | — | — | 0.0 | 0.0 | 0.0 |
| Sugars, total | g | 0.00 | — | — | 0.00 | 0.00 | 0.00 |
| Minerals | | | | | | | |
| Calcium, Ca | mg | 0 | — | — | 0 | 0 | 0 |
| Iron, Fe | mg | 0.00 | — | — | 0.00 | 0.00 | 0.00 |
| Magnesium, Mg | mg | 0 | — | — | 0 | 0 | 0 |
| Phosphorus, P | mg | 0 | — | — | 0 | 0 | 0 |
| Potassuim, K | mg | 0 | — | — | 0 | 0 | 0 |
| Sodium, Na | mg | 0 | — | — | 0 | 0 | 0 |
| Zinc, Zn | mg | 0.00 | — | — | 0.00 | 0.00 | 0.00 |
| Copper, Cu | mg | 0.000 | — | — | 0.000 | 0.000 | 0.000 |
| Selenium, Se | μg | 0.0 | — | — | 0.0 | 0.0 | 0.0 |

-continued

Almond Oil

| Nutrient | Unit | Value per 100.0 g | # of Data Points | Std. Error | tbsp 13.6 g | cup 218 g | tsp 4.5 g |
|---|---|---|---|---|---|---|---|
| Vitamins | | | | | | | |
| Vitamin C, total ascorbic acid | mg | 0.0 | — | — | 0.0 | 0.0 | 0.0 |
| Thiamin | mg | 0.000 | — | — | 0.000 | 0.000 | 0.000 |
| Riboflavin | mg | 0.000 | — | — | 0.000 | 0.000 | 0.000 |
| Niacin | mg | 0.000 | — | — | 0.000 | 0.000 | 0.000 |
| Pantothenic acid | mg | 0.000 | — | — | 0.000 | 0.000 | 0.000 |
| Vitamin B-6 | mg | 0.000 | — | — | 0.000 | 0.000 | 0.000 |
| Folate, total | µg | 0 | — | — | 0 | 0 | 0 |
| Folic acid | µg | 0 | — | — | 0 | 0 | 0 |
| Folate, food | µg | 0 | — | — | 0 | 0 | 0 |
| Folate, DFE | mcg_DFE | 0 | — | — | 0 | 0 | 0 |
| Choline, total | mg | 0.4 | — | — | 0.1 | 0.9 | 0.0 |
| Vitamin B-12 | µg | 0.00 | — | — | 0.00 | 0.00 | 0.00 |
| Vitamin B-12, added | µg | 0.00 | — | — | 0.00 | 0.00 | 0.00 |
| Vitamin A, RAE | mcg_RAE | 0 | — | — | 0 | 0 | 0 |
| Retinol | µg | 0 | — | — | 0 | 0 | 0 |
| Carotene, beta | µg | 0 | — | — | 0 | 0 | 0 |
| Carotene, alpha | µg | 0 | — | — | 0 | 0 | 0 |
| Cryptoxanthin, beta | tig | 0 | — | — | 0 | 0 | 0 |
| Vitamin A, IU | IU | 0 | — | — | 0 | 0 | 0 |
| Lycopene | µg | 0 | — | — | 0 | 0 | 0 |
| Lutein + zeaxanthin | µg | 0 | — | — | 0 | 0 | 0 |
| Vitamin E (alpha-tocopherol) | mg | 39.20 | — | — | 5.33 | 85.46 | 1.76 |
| Vitamin E, added | mg | 0.00 | — | — | 0.00 | 0.00 | 0.00 |
| Vitamin D (D2 + D3) | µg | 0.0 | — | — | 0.0 | 0.0 | 0.0 |
| Vitamin D | IU | 0 | — | — | 0 | 0 | 0 |
| Vitamin K (phylloquinone) | µg | 7.0 | — | — | 1.0 | 15.3 | 0.3 |
| Lipids | | | | | | | |
| Fatty acids, total saturated | g | 8.200 | — | — | 1.115 | 17.876 | 0.369 |
| 4:0 | g | 0.000 | — | — | 0.000 | 0.000 | 0.000 |
| 6:0 | g | 0.000 | — | — | 0.000 | 0.000 | 0.000 |
| 8:0 | g | 0.000 | — | — | 0.000 | 0.000 | 0.000 |
| 10:0 | g | 0.000 | — | — | 0.000 | 0.000 | 0.000 |
| 12:0 | g | 0.000 | — | — | 0000 | 0.000 | 0.000 |
| 14:0 | g | 0.000 | 23 | 0.006 | 0.000 | 0.000 | 0.000 |
| 16:0 | g | 6.500 | 91 | 0.074 | 0.884 | 14.170 | 0.292 |
| 18:0 | g | 1.700 | 90 | 0.077 | 0.231 | 3.706 | 0.076 |
| Fatty acids, total monounsaturated | g | 69.900 | — | — | 9.506 | 152.382 | 3.146 |
| 16:1 undifferentiated | g | 0.600 | 89 | 0.025 | 0.082 | 1.308 | 0.027 |
| 18:1 undifferentiated | g | 69.400 | 91 | 0.426 | 9.438 | 151.292 | 3.123 |
| 20:1 | g | 0.000 | — | — | 0.000 | 0.000 | 0.000 |
| 22:1 undifferentiated | g | 0.000 | — | — | 0.000 | 0.000 | 0.000 |
| Fatly acids, total polyunsaturated | g | 17.400 | — | — | 2.366 | 37.932 | 0.783 |
| 18:2 undifferentiated | g | 17.400 | 91 | 0.394 | 2.366 | 37.932 | 0.783 |
| 18:3 undifferentiated | g | 0.000 | — | — | 0000 | 0.000 | 0.000 |
| 18:4 | g | 0.000 | — | — | 0.000 | 0.000 | 0.000 |
| 20:4 undifferentiated | g | 0.000 | — | — | 0.000 | 0.000 | 0.000 |
| 20:5 n-3 (EPA) | g | 0.000 | — | — | 0.000 | 0.000 | 0.000 |
| 22:5 n-3 (DPA) | g | 0.000 | — | — | 0.000 | 0.000 | 0.000 |
| 22:6 n-3 (DHA) | g | 0.000 | — | — | 0.000 | 0.000 | 0000 |
| Cholesterol | mg | 0 | — | — | 0 | 0 | 0 |
| Phytosterols | mg | 266 | — | — | 36 | 580 | 12 |
| Amino Acids | | | | | | | |
| Tryptophan | g | 0.000 | — | — | 0.000 | 00.00 | 0.000 |
| Threonine | g | 0.000 | — | — | 0.000 | 0000 | 0.000 |
| Isoleucine | g | 0.000 | — | — | 0.000 | 0.000 | 0.000 |
| Leucine | g | 0.000 | — | — | 0.000 | 0.000 | 0.000 |
| Lysine | g | 0.000 | — | — | 0.000 | 0.000 | 0.000 |
| Methionine | g | 0.000 | — | — | 0.000 | 0.000 | 0.000 |
| Cystine | g | 0.000 | — | — | 0.000 | 0.000 | 0000 |
| Phenylalanine | g | 0.000 | — | — | 0.000 | 0.000 | 0.000 |
| Tyrosine | g | 0.000 | — | — | 0.000 | 0.000 | 0.000 |
| Valine | g | 0.000 | — | — | 0.000 | 0.000 | 0.000 |
| Arginine | g | 0.000 | — | — | 0.000 | 00.00 | 0.000 |
| Histidine | g | 0.000 | — | — | 0.000 | 0.000 | 0.000 |
| Alanine | g | 0.000 | — | — | 0.000 | 0.000 | 0.000 |
| Aspartic acid | g | 0.000 | — | — | 0.000 | 0.000 | 0.000 |
| Glutamic acid | g | 0.000 | — | — | 0.000 | 0.000 | 0.000 |

-continued

Almond Oil

| Nutrient | Unit | Value per 100.0 g | # of Data Points | Std. Error | tbsp 13.6 g | cup 218 g | tsp 4.5 g |
|---|---|---|---|---|---|---|---|
| Glycine | g | 0.000 | — | — | 0.000 | 0.000 | 0.000 |
| Proline | g | 0.000 | — | — | 0.000 | 0.000 | 0.000 |
| Serine | g | 0.000 | — | — | 0.000 | 0.000 | 0.000 |
| Other | | | | | | | |
| Alcohol, ethyl | g | 0.0 | — | — | 0.0 | 0.0 | 0.0 |
| Caffeine | mg | 0 | — | — | 0 | 0 | 0 |
| Theobromine | mg | 0 | — | — | 0 | 0 | 0 |

Apricot Kernal Oil

| Nutrient | Unit | Value per 100.0 g | # of Data Points | Std. Error | tbsp 13.6 g | cup 218 g | tsp 4.5 g |
|---|---|---|---|---|---|---|---|
| Proximates | | | | | | | |
| Water | g | 0.00 | — | — | 0.00 | 0.00 | 0.00 |
| Energy | kcal | 884 | — | — | 120 | 1927 | 40 |
| Energy | kJ | 3699 | — | — | 503 | 8064 | 166 |
| Protein | g | 0.00 | — | — | 0.00 | 0.00 | 0.00 |
| Total lipid (fat) | g | 100.00 | — | — | 13.60 | 218.00 | 4.50 |
| Ash | g | 0.00 | — | — | 0.00 | 0.00 | 0.00 |
| Carbohydrate, by difference | g | 0.00 | — | — | 0.00 | 0.00 | 0.00 |
| Fiber, total dietary | g | 0.0 | — | — | 0.0 | 0.0 | 0.0 |
| Sugars, total | g | 0.00 | — | — | 0.00 | 0.00 | 0.00 |
| Minerals | | | | | | | |
| Calcium, Ca | mg | 0 | — | — | 0 | 0 | 0 |
| Iron, Fe | mg | 0.00 | — | — | 0.00 | 0.00 | 0.00 |
| Magnesium, Mg | mg | 0 | — | — | 0 | 0 | 0 |
| Phosphorus, P | mg | 0 | — | — | 0 | 0 | 0 |
| Potassium, K | mg | 0 | — | — | 0 | 0 | 0 |
| Sodium, Na | mg | 0 | — | — | 0 | 0 | 0 |
| Zinc, Zn | mg | 0.00 | — | — | 0.00 | 0.00 | 0.00 |
| Selenium, Se | μg | 0.0 | — | — | 0.0 | 0.0 | 0.0 |
| Vitamins | | | | | | | |
| Vitamin C, total ascorbic acid | mg | 0.0 | — | — | 0.0 | 0.0 | 0.0 |
| Thiamin | mg | 0.000 | — | — | 0.000 | 0.000 | 0.000 |
| Riboflavin | mg | 0.000 | — | — | 0.000 | 0.000 | 0.000 |
| Niacin | mg | 0.000 | — | — | 0.000 | 0.000 | 0.000 |
| Pantothenic acid | mg | 0.000 | — | — | 0.000 | 0.000 | 0.000 |
| Vitamin B-6 | mg | 0.000 | — | — | 0.000 | 0.000 | 0.000 |
| Folate, total | μg | 0 | — | — | 0 | 0 | 0 |
| Folic acid | μg | 0 | — | — | 0 | 0 | 0 |
| Folate, food | μg | 0 | — | — | 0 | 0 | 0 |
| Folate, DFE | mcg_DFE | 0 | — | — | 0 | 0 | 0 |
| Vitamin B-12 | μg | 0.00 | — | — | 0.00 | 0.00 | 0.00 |
| Vitamin A, RAE | mcg_RAE | 0 | — | — | 0 | 0 | 0 |
| Retinol | μg | 0 | — | — | 0 | 0 | 0 |
| Carotene, beta | μg | 0 | — | — | 0 | 0 | 0 |
| Carotene, alpha | μg | 0 | — | — | 0 | 0 | 0 |
| Cryptoxanthin, beta | μg | 0 | — | — | 0 | 0 | 0 |
| Vitamin A, IU | IU | 0 | — | — | 0 | 0 | 0 |
| Lycopene | μg | 0 | — | — | 0 | 0 | 0 |
| Lutein + zeaxanthin | μg | 0 | — | — | 0 | 0 | 0 |
| Vitamin E (alpha-tocopherol) | mg | 4.00 | — | — | 0.54 | 8.72 | 0.18 |
| Lipids | | | | | | | |
| Fatty acids, total saturated | g | 6.300 | — | — | 0857 | 13.734 | 0.284 |
| 4:0 | g | 0.000 | — | — | 0.000 | 0.000 | 0.000 |
| 6:0 | g | 0.000 | — | — | 0.000 | 0.000 | 0.000 |
| 8:0 | g | 0.000 | — | — | 0.000 | 0.000 | 0.000 |
| 10:0 | g | 0.000 | — | — | 0.000 | 0.000 | 0.000 |
| 12:0 | g | 0.000 | — | — | 0.000 | 0.000 | 0.000 |
| 16:0 | g | 5.800 | 54 | 0.117 | 0.789 | 12.644 | 0.261 |
| 18:0 | g | 0.500 | 53 | 0.057 | 0.068 | 1.090 | 0.022 |
| Fatty acids, total monounsaturated | g | 60.000 | — | — | 8.160 | 130.800 | 2.700 |

-continued

| Apricot Kernal Oil | | | | | | | |
|---|---|---|---|---|---|---|---|
| Nutrient | Unit | Value per 100.0 g | # of Data Points | Std. Error | tbsp 13.6 g | cup 218 g | tsp 4.5 g |
| 16:1 undifferentiated | g | 1.500 | 51 | 0.071 | 0.204 | 3.270 | 0.068 |
| 18:1 undifferentiated | g | 58.500 | 54 | 0.763 | 7.956 | 127.530 | 2.632 |
| 20:1 | g | 0.000 | — | — | 0.000 | 0.000 | 0.000 |
| 22:1 undifferentiated | g | 0.000 | — | — | 0.000 | 0.000 | 0.000 |
| Fatty acids, total polyunsaturated | g | 29.300 | — | — | 3.985 | 63.874 | 1.318 |
| 18:2 undifferentiated | g | 29.300 | 54 | 0.688 | 3.985 | 63.874 | 1.318 |
| 18:3 undifferentiated | g | 0.000 | — | — | 0.000 | 0.000 | 0.000 |
| 18:4 | g | 0.000 | — | — | 0.000 | 0.000 | 0.000 |
| 20:4 undifferentiated | g | 0.000 | — | — | 0.000 | 0.000 | 0.000 |
| 20:6 n-3 (EPA) | g | 0.000 | — | — | 0.000 | 0.000 | 0.000 |
| 22:5 n-3 (DPA) | g | 0.000 | — | — | 0.000 | 0.000 | 0.000 |
| 22:6 n-3 (DHA) | g | 0.000 | — | — | 0.000 | 0.000 | 0.000 |
| Cholesterol | mg | 0 | — | — | 0 | 0 | 0 |
| Phytosterols | mg | 266 | — | — | 36 | 580 | 12 |
| Amino Acids | | | | | | | |
| Tryptophan | g | 0.000 | — | — | 0.000 | 0.000 | 0.000 |

| Hazelnut Oil | | | | | | | |
|---|---|---|---|---|---|---|---|
| Nutrient | Unit | Value per 100.0 g | # of Data Points | Std. Error | tbsp 13.6 g | cup 218 g | tsp 4.5 g |
| Proximates | | | | | | | |
| Water | g | 0.00 | — | — | 0.00 | 0.00 | 0.00 |
| Energy | kcal | 884 | — | — | 120 | 1927 | 40 |
| Energy | kJ | 3699 | — | — | 503 | 8064 | 166 |
| Protein | g | 0.00 | — | — | 0.00 | 0.00 | 0.00 |
| Total lipid (fat) | g | 100.00 | — | — | 13.60 | 218.00 | 4.50 |
| Ash | g | 0.00 | — | — | 0.00 | 0.00 | 0.00 |
| Carbohydrate, by difference | g | 0.00 | — | — | 0.00 | 0.00 | 0.00 |
| Fiber, total dietary | g | 0.0 | — | — | 0.0 | 0.0 | 0.0 |
| Sugars, total | g | 0.00 | — | — | 0.00 | 0.00 | 0.00 |
| Minerals | | | | | | | |
| Calcium, Ca | mg | 0 | — | — | 0 | 0 | 0 |
| Iron, Fe | mg | 0.00 | — | — | 0.00 | 0.00 | 0.00 |
| Magnesium, Mg | mg | 0 | — | — | 0 | 0 | 0 |
| Phosphorus, P | mg | 0 | — | — | 0 | 0 | 0 |
| Potassium, K | mg | 0 | — | — | 0 | 0 | 0 |
| Sodium, Na | mg | 0 | — | — | 0 | 0 | 0 |
| Zinc, Zn | mg | 0.00 | — | — | 0.00 | 0.00 | 0.00 |
| Selenium, Se | μg | 0.0 | — | — | 0.0 | 0.0 | 0.0 |
| Vitamins | | | | | | | |
| Vitamin C, total ascorbic acid | mg | 0.0 | — | — | 0.0 | 0.0 | 0.0 |
| Thiamin | mg | 0.000 | — | — | 0.000 | 0.000 | 0.000 |
| Riboflavin | mg | 0.000 | — | — | 0.000 | 0.000 | 0.000 |
| Niacin | mg | 0.000 | — | — | 0.000 | 0.000 | 0.000 |
| Pantothenic acid | mg | 0.000 | — | — | 0.000 | 0.000 | 0.000 |
| Vitamin B-6 | mg | 0.000 | — | — | 0.000 | 0.000 | 0.000 |
| Folate, total | μg | 0 | — | — | 0 | 0 | 0 |
| Folic acid | μg | 0 | — | — | 0 | 0 | 0 |
| Folate, food | μg | 0 | — | — | 0 | 0 | 0 |
| Folate, DFE | mcg_DFE | 0 | — | — | 0 | 0 | 0 |
| Vitamin B-12 | μg | 0.00 | — | — | 0.00 | 0.00 | 0.00 |
| Vitamin A, RAE | mcg_RAE | 0 | — | — | 0 | 0 | 0 |
| Retinol | μg | 0 | — | — | 0 | 0 | 0 |
| Carotene, beta | μg | 0 | — | — | 0 | 0 | 0 |
| Carotene, alpha | μg | 0 | — | — | 0 | 0 | 0 |
| Cryptoxanthin, beta | μg | 0 | — | — | 0 | 0 | 0 |
| Vitamin A, IU | IU | 0 | — | — | 0 | 0 | 0 |
| Lycopene | μg | 0 | — | — | 0 | 0 | 0 |
| Lutein + zeaxanthin | μg | 0 | — | — | 0 | 0 | 0 |
| Vitamin E (alpha-tocopherol) | mg | 47.20 | — | — | 6.42 | 102.90 | 2.12 |

-continued

| Hazelnut Oil | | | | | | | |
|---|---|---|---|---|---|---|---|
| Nutrient | Unit | Value per 100.0 g | # of Data Points | Std. Error | tbsp 13.6 g | cup 218 g | tsp 4.5 g |
| Lipids | | | | | | | |
| Fatty acid, total saturated | g | 7.400 | — | — | 1.006 | 16.132 | 0.333 |
| 4:0 | g | 0.000 | — | — | 0.000 | 0.000 | 0.000 |
| 6:0 | g | 0.000 | — | — | 0.000 | 0.000 | 0.000 |
| 8:0 | g | 0.000 | — | — | 0.000 | 0.000 | 0.000 |
| 10:0 | g | 0.000 | | | 0.000 | 0000 | 0.000 |
| 12:0 | g | 0.000 | 7 | — | — | 0.000 | 0.000 |
| 14:0 | g | 0.100 | 12 | 0.042 | 0.014 | 0.218 | 0.005 |
| 16:0 | g | 5.200 | 111 | 0.055 | 0.707 | 11.336 | 0.234 |
| 18:0 | g | 2.000 | 110 | 0.054 | 0.272 | 4.360 | 0.090 |
| Fatty acids, total monounsaturated | g | 78.000 | — | — | 10.608 | 170.040 | 3.510 |
| 16:1 undifferentiated | g | 0.200 | 104 | 0.010 | 0.027 | 0.436 | 0.009 |
| 18:1 undifferentiated | g | 77.800 | 111 | 0.299 | 10.581 | 169.604 | 3.501 |
| 20:1 | g | 0.000 | 96 | 0.003 | 0.000 | 0.000 | 0.000 |
| 22:1 undifferentiated | g | 0.000 | — | — | 0.000 | 0.000 | 0.000 |
| Fatty acids, total polyunsaturated | g | 10.200 | — | — | 1.387 | 22.236 | 0.459 |
| 18:2 undifferentiated | g | 10.100 | 111 | 0.318 | 1.374 | 22.018 | 0.454 |
| 18:3 undifferentiated | g | 0.000 | 101 | 0.006 | 0.000 | 0.000 | 0.000 |
| 18:4 | g | 0.000 | — | — | 0.000 | 0.000 | 0.000 |
| 20:4 undifferentiated | g | 0.000 | — | — | 0.000 | 0.000 | 0.000 |
| 20:5 n-3 (EPA) | g | 0.000 | — | — | 0.000 | 0.000 | 0.000 |
| 22:5 n-3 (DPA) | g | 0.000 | — | — | 0.000 | 0.000 | 0.000 |
| 22:6 n-3 (DHA) | g | 0.000 | — | — | 0.000 | 0.000 | 0.000 |
| Cholesterol | mg | 0 | — | — | 0 | 0 | 0 |
| Phytosterols | mg | 120 | — | — | 16 | 262 | 5 |
| Amino Acids | | | | | | | |

| Organic Hemp Oil | |
|---|---|
| Test | Result |
| Fatty Acid Profile, % Relative | Area Percent |
| C08:0 Octanoic (Caprylic) | <0.10% |
| C10:0 Decanoic (Capric) | <0.10% |
| C11:0 Undecanoic (Hendecanoic) | <0.10% |
| C12:0 Dodecanoic (Lauric) | <0.10% |
| C13:0 Tridecanoic | <0.10% |
| C14:0 Tetradecanoic (Myristic) | <0.10% |
| C14:1 Tetradecenoic (Myristoleic) | <0.10% |
| C15:0 Pentadecanoic | <0.10% |
| C15:1 Pentadecenoic | <0.10% |
| C16:0 Hexadecanoic (Palmitic) | 5.66% |
| C16:1 Hexadecenoic (Palmitoleic) | 0.14% |
| C16:2 Hexadecadienoic | <0.10% |
| C16:3 Hexadecatrienoic | <0.10% |
| C16:4 Hexadecatetraenoic | <0.10% |
| C17:0 Heptadecanoic (Margaric) | <0.10% |
| C17:1 Heptadecenoic Margaroleic | <0.10% |
| C18:0 Octadecanoic (Stearic) | 2.39% |
| C18:1 Octadecenoic (Oleic) | 9.96% |
| C18:2 Octadecadienoic (Linoleic) | 55.14% |
| C18:3 Octadecatrienoic (Linolenic) | 22.71% |
| C18:4 Octadecatetraenoic | 1.59% |
| C20:0 Eicosanoic (Arachidic) | 0.90% |
| C20:1 Eicosenoic (Gadoleic) | 0.43% |
| C20:2 Eicosadienoic | <0.10% |
| C20:3 Eicosatrienoic | <0.10% |
| C20:4 Eicosatetraenoic (Arachidonic) | <0.10% |
| C20:5 Eicosapentaenoic | <0.10% |
| C21:5 Heneicosapentaenoic | <0.10% |
| C22:0 Docosanoic (Behenic) | 0.37% |
| C22:1 Docosenoic (Erucic) | <0.10% |
| C22:2 Docosadienoic | <0.10% |
| C22:3 Docosatrienoic | <0.10% |
| C22:4 Docosatetraenoic | <0.10% |
| C22:5 Docosapentaenoic | <0.10% |
| C22:6 Docosahexaenoic | <0.10% |

-continued

| Organic Hemp Oil | |
|---|---|
| Test | Result |
| C24:0 Tetracosanoic (Lignoceric) | 0.19% |
| C24:1 Tetracosenoic (Nervonic) | <0.10% |
| Unknown Components | 0.21% |

| Evening Primrose Oil-Cold Pressed | |
|---|---|
| Test | Result |
| Fatty Acid Profile, % Relative | Area Percent |
| C08:0 Octanoic (Caprylic) | <0.10% |
| C10:0 Decanoic (Capric) | <0.10% |
| C11:0 Undecanoic (Hendecanoic) | <0.10% |
| C12:0 Dodecanoic (Lauric) | <0.10% |
| C13:0 Tridecanoic | <0.10% |
| C14:0 Tetradecanoic (Myristic) | <0.10% |
| C14:1 Tetradecenoic (Myristoleic) | <0.10% |
| C15:0 Pentadecanoic | <0.10% |
| C15:1 Pentadecenoic | <0.10% |
| C16:0 Hexadecanoic (Palmitic) | 6.25% |
| C16:1 Hexadecenoic (Palmitoleic) | <0.10% |
| C16:2 Hexadecadienoic | <0.10% |
| C16:3 Hexadecatrienoic | <0.10% |
| C16:4 Hexadecatetraenoic | <0.10% |
| C17:0 Heptadecanoic (Margaric) | <0.10% |
| C17:1 Heptadecenoic Margaroleic | <0.10% |
| C18:0 Octadecanoic (Stearic) | 2.53% |
| C18:1 Octadecenoic (Oleic) | 9.59% |
| C18:2 Octadecadienoic (Linoleic) | 69.97% |
| C18:3 Octadecatrienoic (Linolenic) | 9.56% |
| C18:4 Octadecatetraenoic | <0.10% |
| C20:0 Eicosanoic (Arachidic) | 0.33% |
| C20:1 Eicosenoic (Gadoleic) | 0.40% |

Evening Primrose Oil-Cold Pressed

| Test | Result |
| --- | --- |
| C20:2 Eicosadienoic | <0.10% |
| C20:3 Eicosatrienoic | <0.10% |
| C20:4 Eicosatetraenoic (Arachidonic) | <0.10% |
| C20:5 Eicosapentaenoic | <0.10% |
| C21:5 Heneicosapentaenoic | <0.10% |
| C22:0 Docosanoic (Behenic) | 0.19% |
| C22:1 Docosenoic (Erucic) | 0.19% |
| C22:2 Docosadienoic | <0.10% |
| C22:3 Docosatrienoic | <0.10% |
| C22:4 Docosatetraenoic | <0.10% |
| C22:5 Docosapentaenoic | <0.10% |
| C22:6 Docosahexaenoic | <0.10% |
| C24:0 Tetracosanoic (Lignoceric) | <0.10% |
| C24:1 Tetracosenoic (Nervonic) | 0.10% |
| Unknown Components | 0.30% |

Borage Oil-Cold Pressed

| Test | Result |
| --- | --- |
| Fatty Acid Profile, % Relative | Area Percent |
| C08:0 Octanoic (Caprylic) | <0.10% |
| C10:0 Decanoic (Capric) | <0.10% |
| C11:0 Undecanoic (Hendecanoic) | <0.10% |
| C12:0 Dodecanoic (Lauric) | <0.10% |
| C13:0 Tridecanoic | <0.10% |
| C14:0 Tetradecanoic (Myristic) | <0.10% |
| C14:1 Tetradecenoic (Myristoleic) | <0.10% |
| C15:0 Pentadecanoic | <0.10% |
| C15:1 Pentadecenoic | <0.10% |
| C16:0 Hexadecanoic (Palmitic) | 9.50% |
| C16:1 Hexadecenoic (Palmitoleic) | 0.31% |
| C16:2 Hexadecadienoic | <0.10% |
| C16:3 Hexadecatrienoic | <0.10% |
| C16:4 Hexadecatetraenoic | <0.10% |
| C17:0 Heptadecanoic (Margaric) | <0.10% |
| C17:1 Heptadecenoic Margaroleic | <0.10% |
| C18:0 Octadecanoic (Stearic) | 3.85% |
| C18:1 Octadecenoic (Oleic) | 17.49% |
| C18:2 Octadecadienoic (Linoleic) | 37.52% |
| C18:3 Octadecatrienoic (Linolenic) | 22.57% |
| C18:4 Octadecatetraenoic | 0.17% |
| C20:0 Eicosanoic (Arachidic) | 0.27% |
| C20:1 Eicosenoic (Gadoleic) | 3.76% |
| C20:2 Eicosadienoic | 0.20% |
| C20:3 Eicosatrienoic | <0.10% |
| C20:4 Eicosatetraenoic (Arachidonic) | <0.10% |
| C20:5 Eicosapentaenoic | <0.10% |
| C21:5 Heneicosapentaenoic | <0.10% |
| C22:0 Docosanoic (Behenic) | 0.19% |
| C22:1 Docosenoic (Erucic) | 2.31% |
| C22:2 Docosadienoic | <0.10% |
| C22:3 Docosatrienoic | <0.10% |
| C22:4 Docosatetraenoic | <0.10% |
| C22:5 Docosapentaenoic | <0.10% |
| C22:6 Docosahexaenoic | <0.10% |
| C24:0 Tetracosanoic (Lignoceric) | <0.10% |
| C24:1 Tetracosenoic (Nervonic) | 1.43% |
| Unknown Components | 0.13% |

Organic Flax Oil

| Test | Result |
| --- | --- |
| Fatty Acid Profile, % Relative | Area Percent |
| C08:0 Octanoic (Caprylic) | <0.10% |
| C10:0 Decanoic (Capric) | <0.10% |
| C11:0 Undecanoic (Hendecanoic) | <0.10% |
| C12:0 Dodecanoic (Lauric) | <0.10% |
| C13:0 Tridecanoic | <0.10% |
| C14:0 Tetradecanoic (Myristic) | <0.10% |
| C14:1 Tetradecenoic (Myristoleic) | <0.10% |
| C15:0 Pentadecanoic | <0.10% |
| C15:1 Pentadecenoic | <0.10% |
| C16:0 Hexadecanoic (Palmitic) | 4.81% |
| C16:1 Hexadecenoic (Palmitoleic) | <0.10% |
| C16:2 Hexadecadienoic | <0.10% |
| C16:3 Hexadecatrienoic | <0.10% |
| C16:4 Hexadecatetraenoic | <0.10% |
| C17:0 Heptadecanoic (Margaric) | <0.10% |
| C17:1 Heptadecenoic Margaroleic | <0.10% |
| C18:0 Octadecanoic (Stearic) | 2.98% |
| C18:1 Octadecenoic (Oleic) | 15.01% |
| C18:2 Octadecadienoic (Linoleic) | 15.63% |
| C18:3 Octadecatrienoic (Linolenic) | 60.25% |
| C18:4 Octadecatetraenoic | <0.10% |
| C20:0 Eicosanoic (Arachidic) | 0.11% |
| C20:1 Eicosenoic (Gadoleic) | 0.18% |
| C20:2 Eicosadienoic | <0.10% |
| C20:3 Eicosatrienoic | 0.10% |
| C20:4 Eicosatetraenoic (Arachidonic) | <0.10% |
| C20:5 Eicosapentaenoic | <0.10% |
| C21:5 Heneicosapentaenoic | <0.10% |
| C22:0 Docosanoic (Behenic) | 0.10% |
| C22:1 Docosenoic (Erucic) | <0.10% |
| C22:2 Docosadienoic | <0.10% |
| C22:3 Docosatrienoic | <0.10% |
| C22:4 Docosatetraenoic | <0.10% |
| C22:5 Docosapentaenoic | <0.10% |
| C22:6 Docosahexaenoic | <0.10% |
| C24:0 Tetracosanoic (Lignoceric) | <0.10% |
| C24:1 Tetracosenoic (Nervonic) | <0.10% |
| Unknown Components | 0.37% |

The compositions may further include non-essential fatty acids, such as caprylic acid, capric acid, hendecanoic acid, lauric acid, tetradecanoic acid, myristic acid, myristoleic acid, pentadecanoic acid, pentadecenoic acid, palmitic acid, palmitoleic acid, hexadecanoic acid, hexadecadienoic acid, margaric acid, heptadecenoic acid, stearic acid, oleic acid, and vaccenic acid. Preferably, the amount of non-essential fatty acids in the composition is between about 25% and about 35%.

The medicament of the present invention may be administered to an adult or young adult (adolescent) in need thereof as an ingestible liquid form, or in solid form, such as an oil-based gel capsule, a tablet, or a powder. Administration of the medicament to infants and children under the age of 10 is strongly not recommended. Therefore, the medicament cannot be administered in the form of an infant formula. In a further embodiment, the medicament may be administered as a topical ointment for treatment of cancer, cardiovascular diseases and/or inflammation.

The mixtures of the invention may be formulated into solid nutraceutical or pharmaceutical compositions with suitable, acceptable excipients for oral, enteral, parenteral, intravenous or topical administration. Such excipients are well known in the art. Dosage forms for oral administration include food, baked goods, solid pharmaceutical compositions and nutraceutical formulations, tablets, pills, gels, powder, soft and hard gelatin capsules, two-piece hard gelatin capsules, particles, and the like. Suitable pharmaceutical carriers include any such materials known in the art, e.g., any liquid, gel, solvent, liquid diluent, solubilizer, polymer or the like, which is non-toxic and which does not significantly interact with other components of the formulations in a deleterious manner.

Solid dosage forms for oral administration include, but are not limited to, capsules, tablets, pills, powders, and granules. In such solid dosage forms, the active compounds are mixed with at least one pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents. Solid compositions of a similar type can also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings, such as extended-release, sustained-release, delayed release and immediate-release coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

A dietary composition according to the present invention is any ingestible preparation containing the medicament of the invention mixed with a food product. The food product can be dried, cooked, boiled, lyophilized or baked. Breads, cereals, salads, sandwiches, sprouts, vegetables, animal feed, pills and tablets, are among the vast number of different food products contemplated in the present invention.

Compositions for parenteral injection may comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. The compositions of the present invention can also contain adjuvants such as, but not limited to, preservatives, wetting agents, emulsifying agents, and dispersing agents. It can also be desirable to include isotonic agents such as sugars, sodium chloride, and the like. Prolonged absorption of the injectable pharmaceutical form can be brought about by the inclusion of agents which delay absorption such as aluminum monostearate and gelatin.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Dosage forms for topical administration include, but are not limited to, ointments, creams, emulsions, lotions, gels, sunscreens and agents that favor penetration within the epidermis. Various additives, known to those skilled in the art, may be included in the topical formulations of the invention. Examples of additives include, but are not limited to, solubilizers, skin permeation enhancers, preservatives (e.g., antioxidants), moisturizers, gelling agents, buffering agents, surfactants, emulsifiers, emollients, thickening agents, stabilizers, humectants, dispersing agents and pharmaceutical carriers. Examples of moisturizers include jojoba oil and evening primrose oil. Suitable skin permeation enhancers are well known in the art and include lower alkanols, such as methanol ethanol and 2-propanol; alkyl methyl sulfoxides such as dimethylsulfoxide (DMSO), decylmethylsulfoxide (C10 MSO) and tetradecylmethyl sulfoxide; pyrrolidones, urea; N,N-diethyl-m-toluamide; C2-C6 alkanediols; dimethyl formamide (DMF), N,N-dimethylacetamide (DMA) and tetrahydrofurfuryl alcohol. Examples of solubilizers include, but are not limited to, hydrophilic ethers such as diethylene glycol monoethyl ether (ethoxydiglycol, available commercially as Transcutol®) and diethylene glycol monoethyl ether oleate (available commercially as Softcutol®); polyoxy 35 castor oil, polyoxy 40 hydrogenated castor oil, polyethylene glycol (PEG), particularly low molecular weight PEGs, such as PEG 300 and PEG 400, and polyethylene glycol derivatives such as PEG-8 caprylic/capric glycerides (available commercially as Labrasol®); alkyl methyl sulfoxides, such as DMSO; pyrrolidones, DMA, and mixtures thereof.

The following examples are set forth as representative of specific and preferred embodiments of the present invention. These examples are not to be construed as limiting the scope of the invention in any manner. It should be understood that many variations and modifications can be made while remaining within the spirit and scope of the invention.

EXAMPLES

Example 1

Tumor Growth In Vitro Testing

In a first set of experiments, breast carcinoma cells (ATCC-ZR-75) were grown in vitro in the presence or absence of the medicament. The medicament concentration (725 mg/1.25 ml equaling 580 mg/ml) was diluted with ethanol to a final concentration of 10 mg/ml. The medicament (20 µg/ml) was delivered to the cells. Total cell counts per plate were $2.5 \times 10^6$. Rate of death was determined in the cells grown in the presence of the medicament and compared to the rate of death in control cells grown in the absence of the medicament. As expected, no difference between treatments was detected.

In a second set of experiments, breast carcinoma cells (ATCC-ZR-75) were grown in vitro in RPMI-1640 and seeded into 24-well plates at a concentration of $2\times10^4$ cells/ml. The medicament was added to all wells of one of the plates at a concentration of 20 µg/ml. At the end of a 6 day-period, both of the plates were counted. Cells were lifted with trypsin and all of the wells in one plate pooled. The cells were spun down and counted with a hemacytometer using a trypsin blue exclusion method. Cell samples in replicates of three were taken and live cells vs. dead cells counted for all eight squares of the hemacytometer. The results were averaged. Ninety eight percent (98%) of cancer cells were still alive in both treated and untreated mediums. That is, in vitro cell viability of both treated and untreated specimens were 98%.

As expected, the in vitro experiments above showed no difference between treated vs. untreated control cells.

Example 2

Tumor Growth In Vivo Testing in Mice

In these sets of experiments, 4-6 week old mice were fed with 4.3 g medicament/day five days per week (corresponding to a seven day a week regimen in humans). Mouse Chow was used throughout. The medicament was added to the mice feedings. There were no changes in feeding regimens.

Athymic nude mice were injected with the breast cancer tumor strain MDA-MB-435. Cell line propagation by PSI was by standard in vitro cell expansion methods. Three groups were studied: Group 1 was pretreated with the medicament two weeks prior to tumor implantation. Group 2 was pretreated with the medicament four weeks prior to tumor implantation. Group 3, the control, was not pretreated. Treatment of all animals was by oral gavage, 5 days per week (M-F) until termination. 23 nude female mice were inoculated with $2.5\times10^6$ MDA-MB-435 breast cancer cells subcutaneously. Tumor volumes were monitored by caliper measurement twice per week Animals were sacrificed at 50 days post tumor inoculation. Group 3 consisted of 10 mice whereas both Groups 1 and 2 consisted of 5 mice each. Animals were acclimated for at least 3 days prior to initiation of dosing. Drug dosing was based on bodyweight, with the understanding that human dose is 4,350 mg for a 180-pound person. As mice typically weigh 18-22 grams, each mouse was fed a 100 µl formulation containing 1 µl medicament per day dosage diluted with 99 organic virgin coconut oil (Garden of Life® brand organic extra virgin coconut oil, Jupiter, Fla.). Control animals were fed 100 µl of pure coconut oil with no drug added. The mixture was heated to room temperature and mixed prior to administration. The medicament contained 50% organic evening primrose oil, 33.3% organic flax oil, 10.7% organic pumpkin oil, and 5.95% organic virgin coconut oil. The LA/ALA ratio in the medicament was approximately 2.6/1.0.

Tumor size was based on external caliper measurement of protruding tumor with the primary tumor excised and weighed at termination. Tumor volume was calculated twice each week based on the formula ½ $(a\times b^2)$, where b is the smaller of the two perpendicular diameters. A 20% reduction in tumor growth was considered as statistically significant. All mice were used in the statistical analysis. None were selectively deleted.

Statistical Analysis

A repeated measures analysis of variance was carried out to assess to differences in tumor volume between the three groups over time, focusing on the time period from day 26 and onwards. The analysis showed both a significant difference between groups ($F_{2,119}$=4.06, p=0.02) as well as significant differences in the interaction between groups over time ($F_{18,119}$=2.21, p=0.006). The differences were strongest between group 2 and group 3 ($t_{119}$=−2.78, p=0.006) with group 2 having significantly reduced tumor volumes across the time period as a whole. The differences between group 1 and group 3 were not as strong across the whole time period of analysis ($t_{119}$=−1.52, p=0.13).

| Test of Group and Group by Time Differences | | | | |
|---|---|---|---|---|
| Effect | Num DF | Den DF | F Value | p-value |
| GROUP | 2 | 119 | 4.06 | 0.0196 |
| GROUP * time | 18 | 119 | 2.21 | 0.0059 |

| Group by Group comparisons | | | | | | | |
|---|---|---|---|---|---|---|---|
| Effect | GROUP | GROUP | Estimate | Standard Error | DF | T Value | p-value |
| GROUP | 1 | 2 | 22.0159 | 20.0856 | 119 | 1.10 | 0.2752 |
| GROUP | 1 | 3 | −26.3754 | 17.3946 | 119 | −1.52 | 0.1321 |
| GROUP | 2 | 3 | −48.3913 | 17.3946 | 119 | −2.78 | 0.0063 |

The data thus obtained were subject to repeated measure analysis of variance. The results are shown in the table below:

Mean differences in tumor volumes between groups over 26-50 days.

| | Mean difference in decrease in tumor size | Standard Error | 95% Confidence Interval | |
|---|---|---|---|---|
| Group 1 vs Group 3 | −26.38 | 17.39 | −60.46 | 7.70 |
| Group 2 vs Group 3 | −48.39 | 17.39 | −82.47 | −14.31 |
| Group 1 vs Group 2 | 22.01 | 20.09 | −17.37 | 61.39 |

Discussion of Results

FIG. 1 graphically depicts measured tumor volumes among the three groups of test mice between 26 and 50 days following tumor implantation. Major differences in tumor growth were seen between Group 2 (4-week pre-treat drug) and Group 3 (the control), and, to a lesser extent, between Group 1 (4-week pre-treat drug) and Group 3 (the control). An averaged 24.1% reduction in tumor size was detected in Group 2 26 days after implantation as compared to the control group, and an averaged 30% reduction in tumor size was detected in Group 2 50 days after implantation, as compared to the control group. These results clearly shows that the longer the pretreatment with the medicament, the better is the protection against tumor. These results also indicate that adequate pretreatment with the medicament of the invention effectively prevents or inhibits cancer development.

Group 3 (control) showed a cancer tumor mean growth volume rate of 135 cc to 270 cc occurring over 24 days. Group 2 showed a similar pattern in growth volume rate, yet the mean absolute size was significantly different (from 105 cc to 210 cc). In Group 2 the growth volume was 42 cc versus a growth volume of 60 cc in Group 3. The difference in growth volume between the two groups equals to a 42.8% decrease in tumor growth following pretreatment with the medicament.

It is expected that the efficacy of the medicament in humans will be even higher than in mice because of the seven day weekly regimen, rather than a five day weekly regimen in mice, and because the formulations fed to mice are specifically formulated for humans.

Example 3

Cardiovascular Disease In Vivo Testing in Human Subjects

To evaluate the effect of the medicament on preventing and reversing cardiovascular disease, long-term and short-term studies were performed. Specifically, the effect of the medicament was evaluated for (a) long-term use in subjects taking the medicament for an average of approximately 24 months; (b) short-term use in subjects taking the medicament for an average of approximately 3 months; and (c) in place of fish oil only supplement in subjects who stopped taking the fish oil only supplement and replaced the fish oil only supplement with the medicament of the invention for an average of approximately 3.4 months.

The subjects (all adults) were administered a standard dose of 2.9 grams (2,900 mg) of medicament daily, in both liquid and capsule form. The medicament was administered either all at once or split into 2 doses of 1450 mg each. The medicament contained either 16.5% evening primrose oil, 34.5% flax oil, 16.5% pumpkin oil, 5.5% coconut oil, 13.5% sunflower oil and 13.5% safflower oil, or 16.5% evening primrose oil, 34.5% flax oil, 22.5% pumpkin oil, 5.5% coconut oil and 22.5% sunflower oil. No differences between the two kinds of medicament were noticed in the results of the study.

During the trial the subjects did not change their diet or exercise habits. Healthy subjects as well as subjects with existing diabetes or cardiovascular pre-conditions, took part in the trial.

Long-Term Study 33 subjects, 22 females and 11 males, 35-75-years-old (average age 62-years-old) completed the study by taking the medicament for timeframes of approximately 3 months to 48 months. Half of the subjects took the medicament for a period under two years, and half of the subjects took the medicament for a period of over two years and less than four years, with the average being two years. The subjects' arteries were examined by DPA and compared to accepted waveforms for age. The results are shown in the table below:

| Patient | Sex | Age | Biological Age | Visit Date | Type | Age of Arteries | Months Treatment | Smoker | Additional Medications | Fish Oil Supplement |
|---|---|---|---|---|---|---|---|---|---|---|
| 1 | M | 64 | 57 | 16 Nov. 2009 | D | 71 | 36 | No | No | No |
| 2 | M | 68 | 33 | 20 Nov. 2009 | B | 46 | 36 | No | No | No |
| 3 | M | 53 | 35 | 05 Nov. 2009 | B | 59 | 48 | No | No | No |
| 4 | M | 35 | 32 | 13 Nov. 2009 | B | 31 | 48 | No | No | No |
| 5 | M | 37 | 32 | 09 Nov. 2009 | B | 34 | 48 | Yes | No | No |
| 6 | F | 70 | 57 | 12 Nov. 2009 | D | 76 | 6 | No | No | No |
| 7 | F | 59 | 34 | 11 Nov. 2009 | B | 51 | 8 | No | Yes | No |
| 8 | F | 67 | 57 | 17 Nov. 2009 | D | 76 | 6 | No | No | No |
| 9 | F | 67 | 56 | 10 Nov. 2009 | D | 73 | 6 | No | No | No |
| 10 | F | 74 | 77 | 20 Nov. 2009 | F | 78 | 48 | No | Yes | No |
| 11 | M | 65 | 31 | 08 Dec. 2009 | B | 25 | 48 | No | No | No |
| 12 | F | 75 | 78 | 20 Nov. 2009 | F | 80 | 4 | No | No | No |
| 13 | F | 59 | 46 | 10 Nov. 2009 | C | 69 | 48 | No | Yes | No |
| 14 | F | 62 | 57 | 16 Nov. 2009 | D | 74 | 10 | No | Yes | No |
| 15 | M | 74 | 35 | 10 Nov. 2009 | B | 59 | 48 | No | No | No |
| 16 | M | 67 | 56 | 03 Nov. 2009 | D | 64 | 48 | No | No | No |
| 17 | F | 55 | 77 | 12 Nov. 2009 | F | 80 | 48 | No | Yes | No |
| 18 | M | 68 | 68 | 19 Nov. 2009 | E | 78 | 6 | No | Yes | No |
| 19 | M | 54 | 55 | 16 Nov. 2009 | D | 59 | 5 | No | No | No |
| 20 | M | 52 | 33 | 28 Nov. 2009 | B | 46 | 5 | No | No | No |
| 21 | F | 70 | 56 | 18 Nov. 2009 | D | 66 | 48 | No | No | No |
| 22 | F | 64 | 77 | 16 Nov. 2009 | F | 80 | 48 | No | No | No |
| 23 | F | 62 | 35 | 28 Nov. 2009 | B | 57 | 48 | No | Yes | No |
| 24 | F | 72 | 78 | 17 Nov. 2009 | F | 80 | 6 | No | No | No |
| 25 | F | 60 | 67 | 11 Nov. 2009 | E | 76 | 7 | No | No | No |
| 26 | M | 70 | 58 | 10 Nov. 2009 | D | 80 | 6 | No | No | No |
| 27 | F | 60 | 58 | 02 Dec. 2009 | D | 80 | 6 | No | Yes | No |
| 28 | F | 62 | 35 | 08 Dec. 2009 | B | 58 | 48 | No | Yes | No |
| 29 | M | 51 | 56 | 06 Nov. 2009 | D | 62 | 8 | No | Yes | No |
| 30 | F | 35 | 32 | 12 Nov. 2009 | B | 31 | 24 | No | No | No |
| 31 | F | 56 | 56 | 10 Nov. 2009 | D | 67 | 3 | No | Yes | No |
| 32 | F | 67 | 33 | 20 Nov. 2009 | B | 43 | 24 | No | Yes | No |
| 33 | F | 62 | 57 | 05 Nov. 2009 | D | 76 | 24 | No | Yes | No |

The results of the study showed improvement in seventy-three percent (73%) of the subjects. Overall, the mean age of arteries (flexibility) was 8.82 years less than chronological age. These results were highly significant, as indicated by a p value of 15 in 1,000 (p=0.0015). In one subject the age of the arteries was 39 years less than the chronological age.

The data above translated into a Number Needed to Treat (NNT) of 1.4 (34 total patients/25 successful outcomes defined as an improvement showing "biological age" of subject cardiovascular system to be less than their physical age). NNT quantifies how many patients need to be treated to see one success. An NNT of less than 50 is considered extremely good. Twenty-five out of thirty-four patients had biological ages less than their physical age. Included were 5 known diabetic subjects and 1 subject with known significant pre-existing cardiovascular disease. Three (3) of the five (5) diabetic subjects had waveforms expected of a subject having an age inferior to their biological ages. The NNT of medicament success in the diabetic population was 5/−3=1.7.

These results clearly show that the medicament is effective in reversing existing cardiovascular and diabetic pre-conditions in subjects in need thereof Statistical results:
Analysis by Alex Kiss, Ph.D. (statistics) - Jan. 21, 2010
Analysis Variable: agediff

| N | Minimum | Maximum | Mean | Std Dev | Pr > \|t\| |
|---|---|---|---|---|---|
| 34 | −39.00 | 22.00 | −8.82 | 14.84 | 0.0015 |

Short-Term Study

The short-term effects of the medicament of the invention were evaluated in 16 subjects, 9 females and 7 males, ages 46-84, with an average age of 64-years-old. The subjects were administered a daily dose of 2,900 mg of medicament, and the effect of the medicament was evaluated after a period averaging three months. At the end of three months, an average improvement of 7.2 years (a lower biological cardiovascular age than the physical age) was detected in the subjects ($p=0.0099$). One of the two (2) diabetic subjects showed an improvement, providing an NNT of 2.0 in the diabetic population.

Analysis by Alex Kiss, Ph.D. (statistics) -
Mar. 26, 2010 Analysis Variable: agediff

| N | Mean | Std Dev | Pr > \|t\| |
|---|---|---|---|
| 16 | −7.24 | 10.19 | 0.0099 |

Seven of the 16 subjects showed significant improvement, with an NNT of 2.3. These data clearly show that the medicament is highly effective in preventing and treating cardiovascular diseases in affected subjects as well as in diabetic subjects.

Comparison of the Medicament to Fish Oil Only Supplements

The effects of the medicament was evaluated in subjects who ceased taking fish oil only supplements and were administered a daily dosage of 2,900 mg in place of the fish oil only supplements for an average period of 3.4 months. The effects of the medicament were evaluated by detecting pulse wave velocity arterial flexibility in five (5) male subjects and one (1) female subject aged 58-71, with an average age of 64.5-years-old. The results of the study are shown in the table below:

| Subject | Chronological Age | Biological Age With Fish Oil Only | Biological Age With Medicament | Length of Treatment (Months) |
|---|---|---|---|---|
| A | 63 | 56 | 34 | 4 |
| B | 69 | 67 | 57 | 1 |
| C | 65 | 54 | 46 | 5.5 |
| D | 61 | 56 | 35 | 1 |
| E | 71 | 35 | 34 | 4 |
| F | 58 | 33 | 33 | 4.5 |

On average, the medicament quickly improved the cardiovascular system's arterial flexibility by over 10 years (younger) in the subjects. Four (4) subjects showed improvement, and in two (2) subjects no changes were detected. No subject showed worsening of conditions after taking the medicament. Results were statistically significant ($p=0.04$). Of the five (5) subjects diagnosed with high cholesterol levels who stopped taking fish oil only supplements and took the medicament instead, four (4) showed an improvement in their cardiovascular biological ages. The NNT for subjects with high cholesterol was 1.25. One subject diagnosed with diabetes and high cholesterol also showed improvement. Medicament intervention resulted in an NNT of 1.5 in 66% of subjects. These results clearly show that the medicament is superior to fish oil only supplements in preventing and reversing cardiovascular disease.

Example 4

Tissue Repair In Vivo Testing in Human Subjects

Repair of flogistic resolution, edema and scar tissue is essential in post-operative tissue recovery. Antibiotics and anti-flogistic drugs are routinely used for tissue healing after plastic surgery.

In order to determine the effect of the medicament of the invention in post-plastic surgery recovery, five subjects were administered the medicament from 15 days prior to surgery and kept on the medicament for 30 days afterward. All five patients showed remarkably improved and faster tissue repair with better recovery. In particular, the results showed faster healing, a decrease in inflammation, a decrease in scar tissue and a decrease in the level of pain reported by the patient.

Those of skill in the art will recognize that numerous modifications and changes may be made to the exemplary designs and embodiments described herein and that the invention is not limited to such embodiments.

What is claimed is:

1. A medicament comprising a composition comprising a blend of oils comprising linoleic acid (LA) and α-linolenic acid (ALA) in a LA/ALA ratio that is greater than 1:1 and less than 5:1, wherein the blend of oils in the composition further comprises: between about 15% and about 85% of gamma linolenic acid (GLA)-containing oils, and wherein (a) the blend of oils in the composition further comprise eicosapentaenoic acid (EPA)- and/or docosahexaenoic acid (DHA)-containing oils; (b) the amount of EPA, DHA, or the combined amount of EPA and DHA in the composition is less than the amount of GLA; and (c) the ratio of GLA to the amount of EPA, DHA, or the combined amount of EPA and DHA is greater than 1:1 and less than 5:1.

2. The medicament of claim 1, wherein the amount of EPA and/or DHA is from about 1.0 mg to about 15.0 mg.

3. The medicament of claim 1, wherein the EPA:DHA ratio is from about 1:1 to about 3:1.

4. The medicament of claim 1, wherein the composition comprises from 0.1% to 25% w/v GLA.

5. The medicament of claim 1, wherein the EPA/DHA containing oils are marine oils.

6. The medicament of claim 1, wherein the oils in the composition are selected from the group consisting of: chia, kukui, echium, hemp, evening primrose, flax, pumpkin, soybean, walnut, wheat germ, safflower, sunflower, grape seed, borage, black current, corn, sesame, rice bran, cottonseed, peanut, almond, olive, avocado, coconut, palm kernel, beech, brazil, pecan, pistachio, hickory, filbert, macadamia, cashew, perilla and neem.

7. The medicament of claim 1, wherein the LA-containing, ALA-containing and GLA-containing oils are chemically unprocessed.

8. The medicament of claim 1, wherein the plants or seeds from which the LA-containing, ALA-containing and GLA-containing oils are extracted are not treated with pesticides or additives.

9. The medicament of claim 1, wherein the composition comprises no more than 70% w/v of a non-essential fatty acid comprising 6 to 18 carbons.

10. The medicament of claim 1, wherein the LA/ALA ratio is within a range from 2:1 to 4:1.

11. The medicament of claim 1, wherein the composition comprises: between about 15% w/v and about 85% w/v of evening primrose oil, borage oil, black current oil or other GLA-containing oils and between about 0.1% w/v and about 25% w/v of gamma-linolenic acid (GLA); wherein at least 20% of the composition comprises linoleic acid (LA) and α-linolenic acid (ALA) in a LA/ALA ratio that is greater than 1:1 and less than 5:1; and wherein the amount of the DHA and/or EPA in the composition is not greater than 20% w/v.

12. The medicament of claim 11, wherein the DHA and the EPA are in natural triglyceride form.

13. The medicament of claim 1, wherein at least 50% of the composition by weight comprises linoleic acid (LA) and α-linolenic acid (ALA) in a LA/ALA ratio that is greater than 1:1 and less than 5:1.

14. The medicament of claim 1, wherein the composition is in form of a tablet, dragee, gel, powder, soft capsule, hard gelatin capsule, two-piece hard gelatin capsule, particle, pill, granule, baked good, solution, suspension or dispersion for oral or parenteral administration.

15. A method of treating a disease selected from the group consisting of breast cancer, cardiovascular disease and inflammation in a subject in need thereof comprising administering to the subject the medicament of claim 1, wherein the medicament is administered orally, enterally, parenterally, or intravenously.

16. The medicament of claim 1, wherein the composition comprises less than 0.5% w/v arachidonic acid.

* * * * *